United States Patent
Ortiz

(10) Patent No.: US 7,547,311 B2
(45) Date of Patent: Jun. 16, 2009

(54) SPRING-BASED FIRING MECHANISM FOR ANASTOMOTIC RING APPLIER

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 658 days.

(21) Appl. No.: 11/120,886

(22) Filed: May 3, 2005

(65) Prior Publication Data

US 2006/0253136 A1    Nov. 9, 2006

(51) Int. Cl.
*A61B 17/10* (2006.01)
(52) U.S. Cl. ..................................... 606/142
(58) Field of Classification Search ............. 606/153, 606/154–156; 623/1.11, 1.12
See application file for complete search history.

(56) References Cited

U.S. PATENT DOCUMENTS

| | | | |
|---|---|---|---|
| 4,577,631 A * | 3/1986 | Kreamer | 606/108 |
| 5,702,419 A * | 12/1997 | Berry et al. | 623/1.13 |
| 5,855,312 A | 1/1999 | Toledano | |
| 6,171,321 B1 | 1/2001 | Gifford et al. | |
| 6,451,029 B1 | 9/2002 | Yeatman | |
| 6,471,713 B1 * | 10/2002 | Vargas et al. | 606/153 |
| 6,485,496 B1 | 11/2002 | Suyker et al. | |
| 2003/0032967 A1 | 2/2003 | Park et al. | |

FOREIGN PATENT DOCUMENTS

| | | |
|---|---|---|
| EP | 0639350 | 4/1998 |
| EP | 1520526 | 4/2005 |
| EP | 1520527 | 4/2005 |
| EP | 1520529 | 4/2005 |
| EP | 1520531 | 4/2005 |
| EP | 1520532 | 4/2005 |

OTHER PUBLICATIONS

Office Action dated Jan. 4, 2006, for U.S. Appl. No. 10/675,497, filed Sep. 30, 2003.
European Search Report, Aug. 29, 2006, Application No. 06252328.7, pp. 1-8.

* cited by examiner

*Primary Examiner*—(Jackie) Tan-Uyen T Ho
*Assistant Examiner*—Gregory A Anderson
(74) *Attorney, Agent, or Firm*—Frost Brown Todd LLC

(57) ABSTRACT

A surgical instrument for applying an anastomotic ring device comprises a handle that is connected to an anastomotic ring deployment mechanism by an elongate shaft. The instrument also comprises an actuation mechanism that is configured to apply an actuating force to the ring deployment mechanism to deploy an anastomotic ring. In one embodiment, the actuation mechanism applies a compressive force to deploy the anastomotic ring by drawing opposing ends of a ring deployment mechanism together. The actuation mechanism may comprise a spring or other resilient member moveable from a first position to a second position in order to actuate the ring deployment mechanism. A mechanism is operable to maintain the spring in the first position, while permitting the spring to move to the second position in response to user input. A mechanism is operable to dislodge the spring.

19 Claims, 12 Drawing Sheets

SPRING-BASED FIRING MECHANISM FOR ANASTOMOTIC RING APPLIER

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

Many conventional applier devices require that an actuation force be transmitted from the operating handle to the distal ring deployment mechanism. While this force is generally relatively small, even a low force may be prohibitive when it must be transmitted to the end of a long flexible or detached structure. Also, when the elongated shaft of the applier device includes one or more flexible joints, the control wires generally used to transmit actuating force through the flexible joints might be susceptible to buckling or twisting. In addition, with some applier devices that include flexible joints, force transmission through wires controlling the ring deployment mechanism might have the undesirable effect of straightening the flexible joint from its intended orientation due to increased tension in the transmission wires.

Consequently, it may be desirable to have an anastomotic ring applier device that is capable of deploying an anastomotic ring without requiring that a large actuating force be transferred from a proximal portion of the device to a distal portion thereof.

BRIEF SUMMARY OF THE INVENTION

Embodiments of the invention provide an anastomotic ring applier device that is capable of deploying an anastomotic ring without requiring a large actuating force to be transmitted from the proximal portion of the device to the distal portion thereof. Further, because only a very small actuating force is transmitted distally, the force transmission may not affect the desired orientation of any flexible joints which the device may comprise.

In one embodiment, a surgical instrument comprises a handle connected to a ring deployment mechanism by an elongate shaft. The ring deployment mechanism comprises a proximal portion, a distal portion and a central portion. The device also comprises an actuation mechanism operable to compress the distal portion and the central portion of the ring deployment mechanism towards the proximal portion in order to deploy an anastomotic ring. This embodiment allows the user to deploy an anastomotic ring by using a distally-located actuating mechanism that compresses the ring deployment mechanism.

In another embodiment, a surgical instrument for applying an anastomotic ring device comprises a handle connected by an elongate shaft to a ring deployment mechanism. The ring deployment mechanism is configured to receive and deploying an anastomotic ring. The instrument further comprises a spring, which is moveable from a first position to a second position. The spring is operable to actuate the ring deployment mechanism as it moves to the second position. This embodiment permits a user to actuate a ring deployment mechanism without requiring the user to input a large actuating force.

In yet another embodiment, a device comprises a handle including an operating control moveable from a first position to a second position. The device further comprises an elongate shaft connecting the handle to a ring deployment mechanism that is configured to receive and deploy an anastomotic ring under an actuating force. The device further comprises an actuation member that is configured to store the actuating force. The actuation member is operable to apply the actuating force to the ring deployment mechanism when the operating control moves from the first position to the second position. This embodiment allows the user to trigger a stored force to actuate the ring deployment mechanism, rather than requiring the user to input an actuation force that must be transmitted along the full length of the elongate shaft.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF EMBODIMENTS OF THE INVENTION

Figure 1:
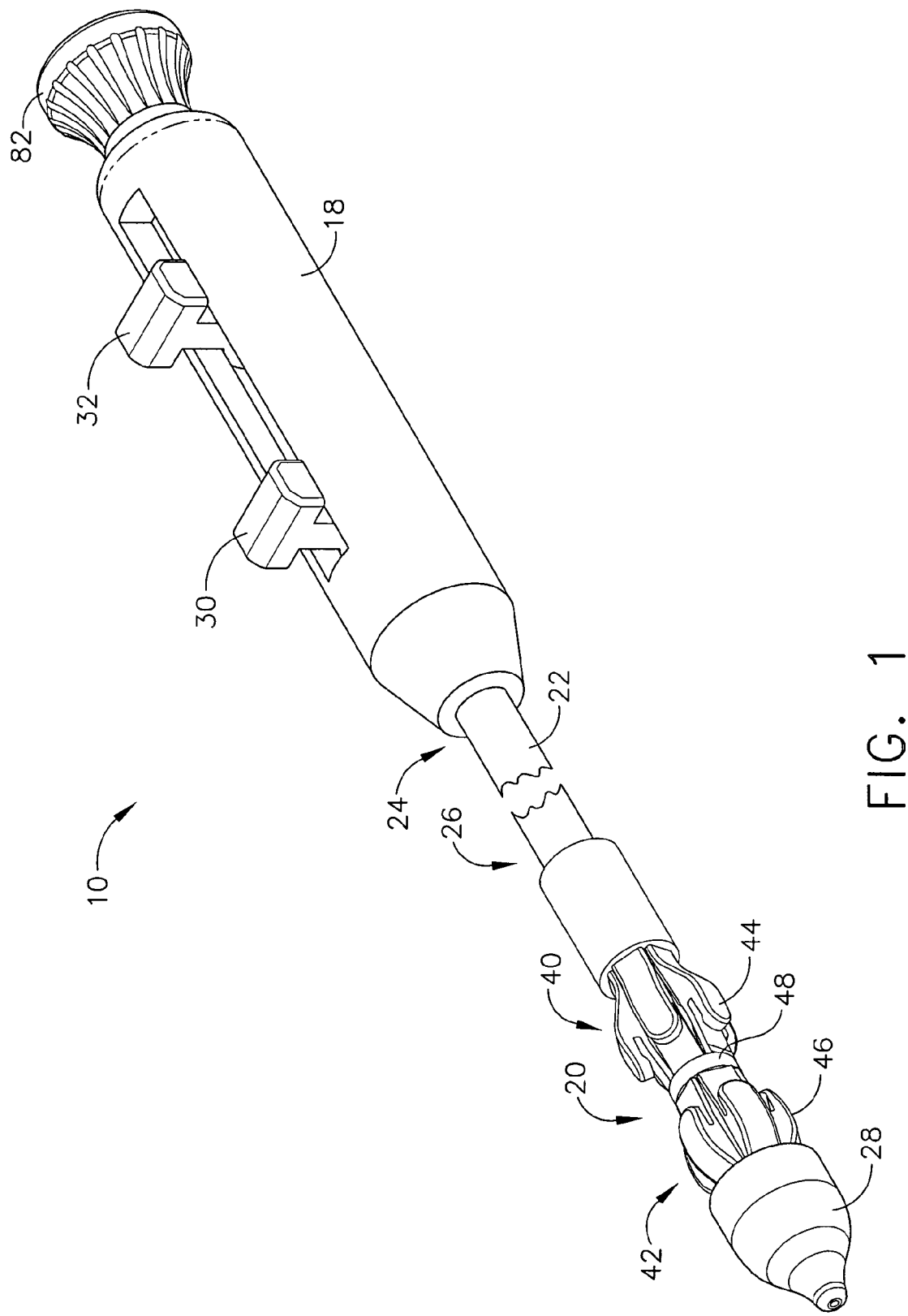
FIG. 1 is a perspective view of an anastomotic ring applier device, shown with a ring deployment mechanism in an unactuated position.
Figure 2:
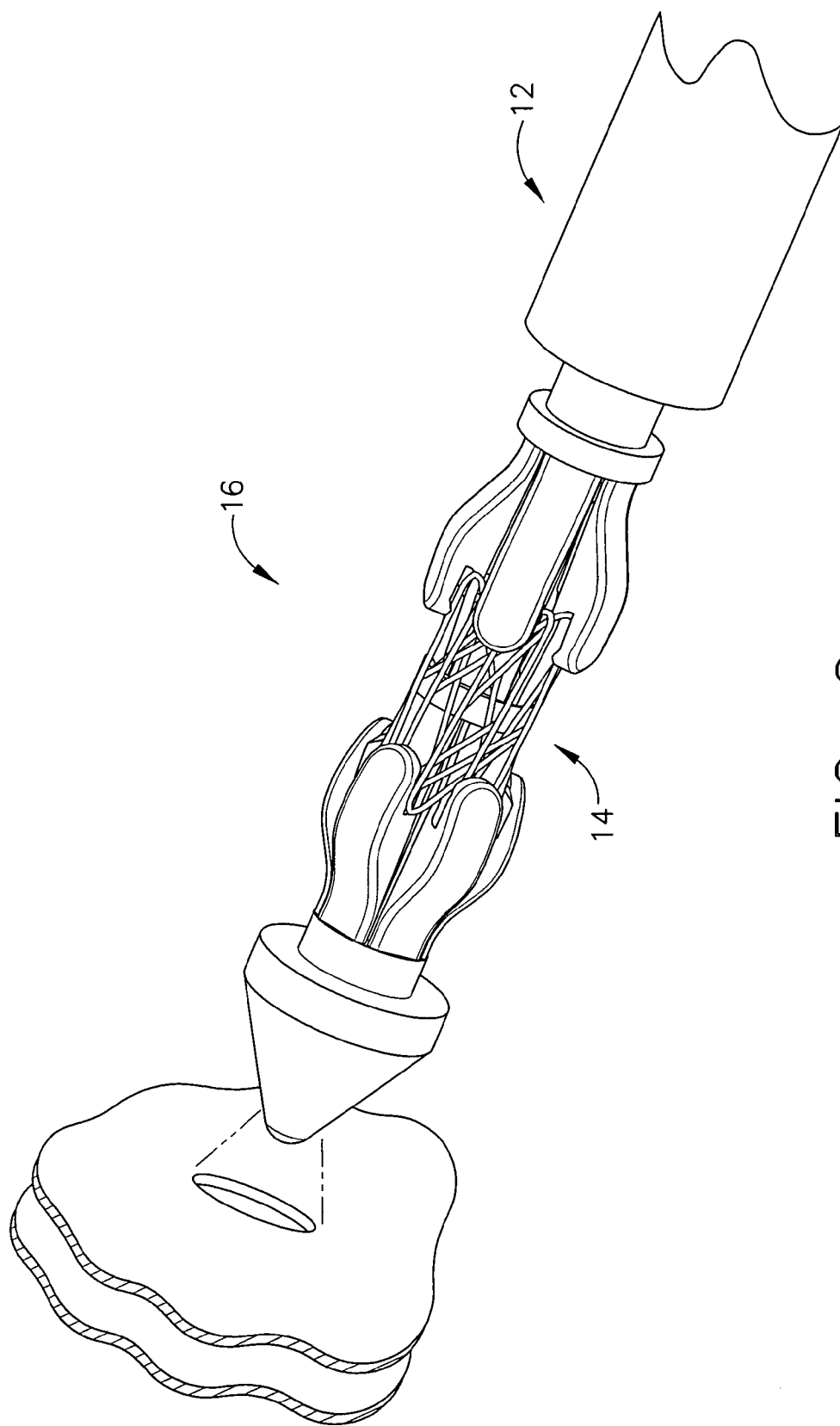
FIG. 2 is a partial perspective view of the distal portion of an anastomotic ring applier device holding an anastomotic ring in an unactuated position.
Figure 3:
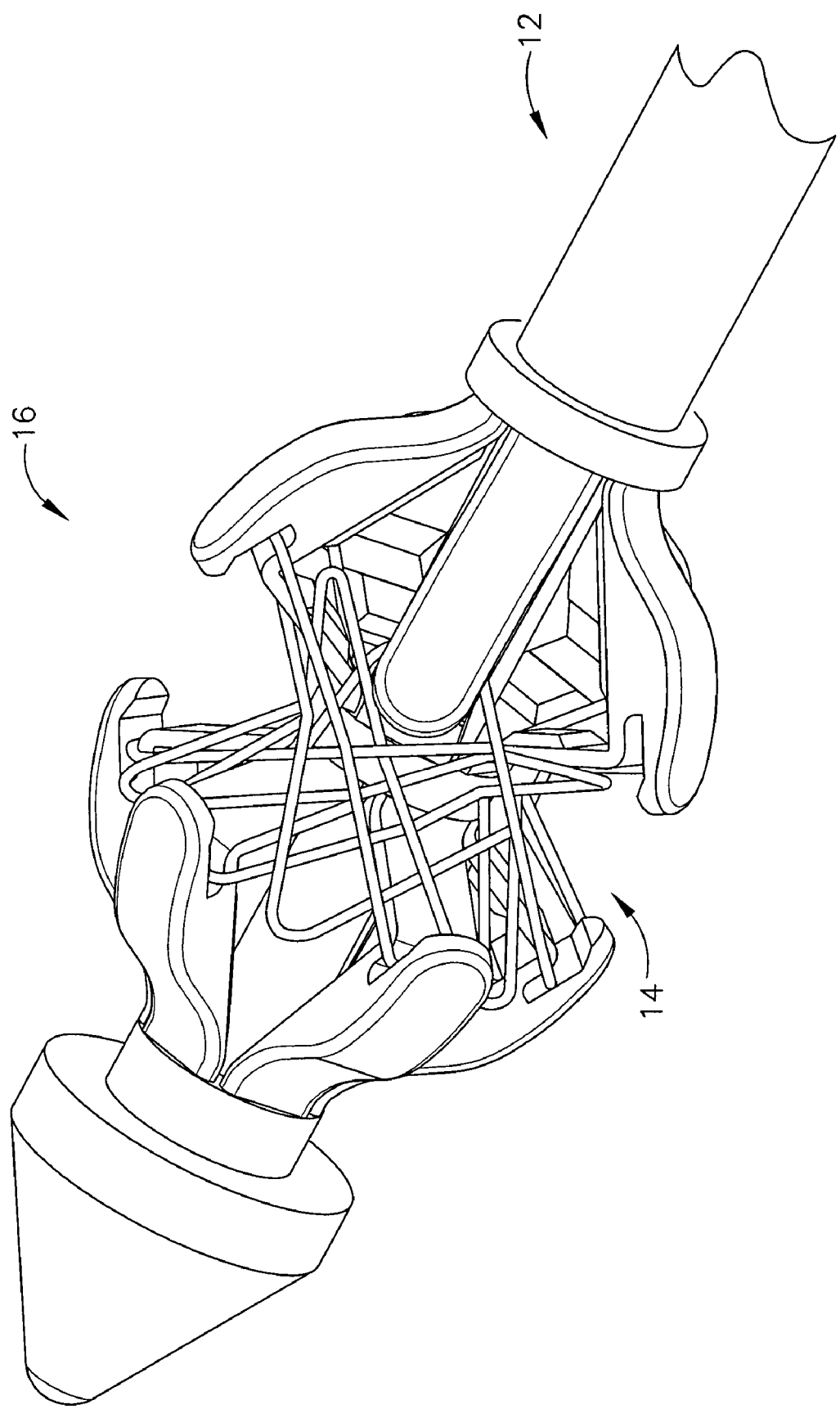
FIG. 3 is a partial perspective view of the distal portion of the device of FIG. 2 holding an anastomotic ring in the actuated position.
Figure 4:
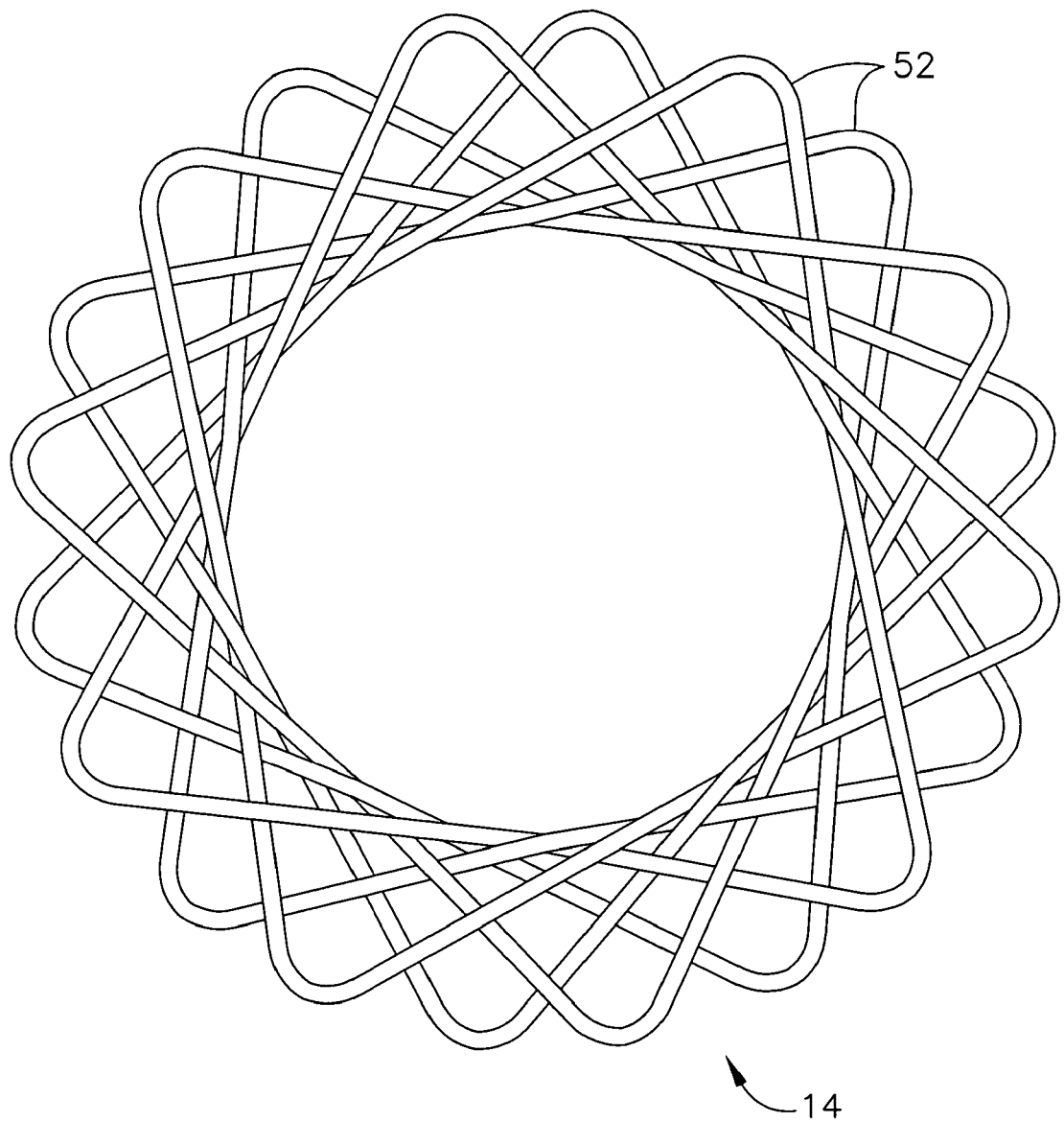
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Referring to FIGS. 1 and 5-7, a handle 18 is shown connected to a ring deployment mechanism 20 by an elongated shaft 22 having a proximal portion 24 and a distal portion 26. Shaft 22 may be rigid, flexible, malleable, or have any other properties. Applier 10 further includes a tip 28 distal of ring deployment mechanism 20. First and second actuator members 30, 32 are included on handle 18. As will be described in detail below, actuator members 30, 32 are operable to control operation of ring deployment mechanism 20 to deploy anastomotic ring 14.

Figure 8:
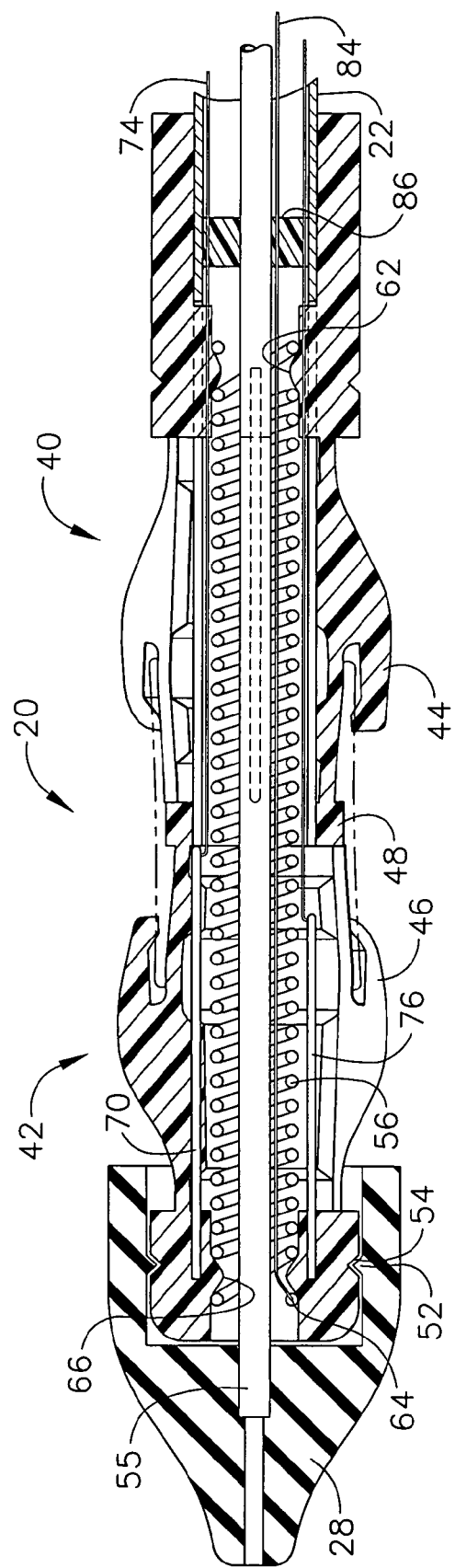
FIG. 8 is a cross-sectional view of the ring deployment mechanism of the device of FIG. 1 in the unactuated position.

As shown in FIG. 8, ring deployment mechanism 20 comprises a proximal portion 40 and a distal portion 42. Proximal portion 40 comprises proximal fingers 44, and distal portion 42 similarly comprises distal fingers 46. Both proximal and distal fingers 44, 46 are in a double-hinged relationship with a mid-ring 48 of deployment mechanism 20. Proximal portion 40 is fixedly attached to shaft 22. Fingers 44, 46 are configured to hold an anastomotic ring 14 by engaging petals 51 prior to and during deployment of the anastomotic ring, and release petals 51 upon deployment of the anastomotic ring. Of course, any other suitable configuration for ring deployment mechanism 20 may be used.

Tip 28 is connected to distal portion 42 of deployment mechanism 20. As shown in FIGS. 8-11, a rib 52 of tip 28 is configured to mate with a recess 54 of distal portion 42. However, it will be appreciated that tip 28 may be affixed to ring deployment mechanism 20 in numerous alternative ways. In the present example, applier 10 further comprises a rod 55, which passes through shaft 22 and terminates in tip 28. Rod 55 may be rigid, flexible, or have other properties. Other suitable tip 28 configurations will be apparent to those of ordinary skill in the art.

Figure 12:
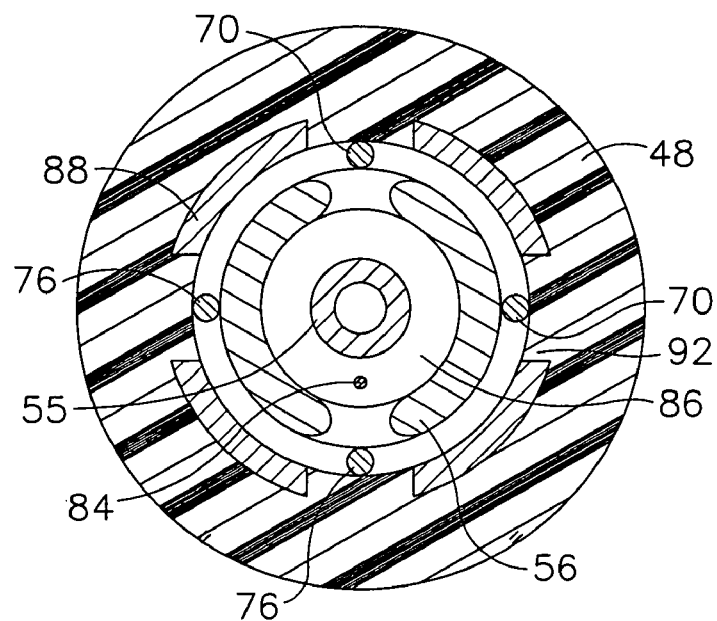
FIG. 12 is a cross-sectional view taken along Plane 12 of the device of FIG. 10.
Figure 13:
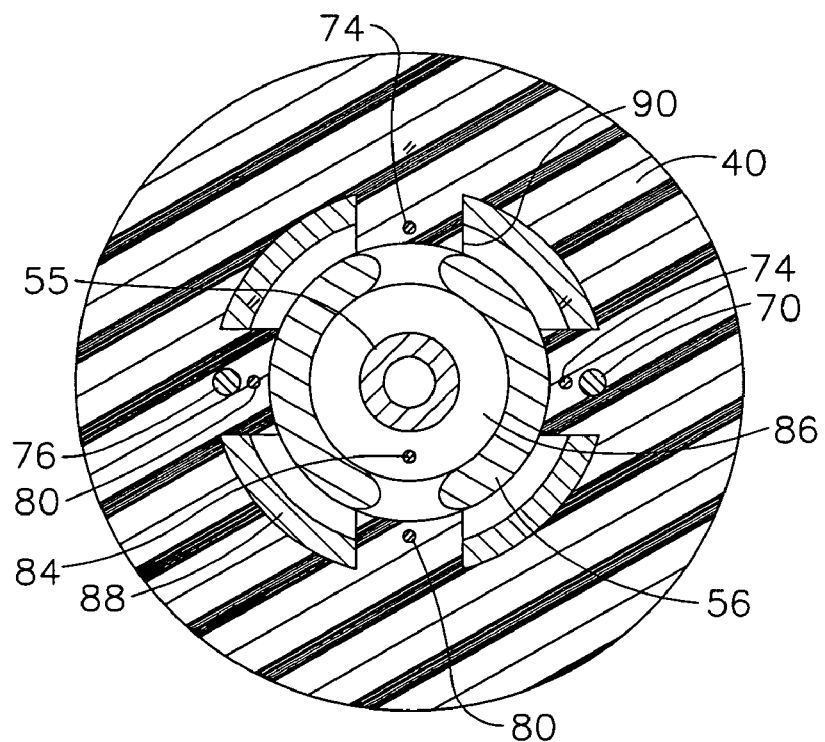
FIG. 13 is a cross-sectional view taken along Plane 13 of the device of FIG. 10.

Shaft 22 further comprises bushings 86, which are disposed within shaft 22 and about rod 55. As shown in FIGS. 12 (in which proximal fingers 44 are omitted) and 13, a distal portion of shaft 22 comprises longitudinal extremities 88, which are separated by longitudinal slots. The proximal portion 40 of deployment mechanism 20 has rib members 90, which extend radially inward, and are sized and spaced to fit between extremities 88. Similarly, mid-ring 48 of deployment mechanism 20 has rib members 92, which extend radially inward, and are sized and spaced to fit between extremities 88. In the present example, the fit between extremities 88 and rib members 90, 92 is such that rotation of deployment mechanism 20 with respect to shaft 22 is substantially prevented.

With continued reference to FIG. 8, applier 10 of the present example includes an actuation mechanism that is operable to apply an actuating force to ring deployment mechanism 20. In one embodiment, the actuation mechanism comprises an extension spring 56. A proximal portion of spring 56 is in communication with proximal portion 40 of deployment mechanism 20. In the present example, proximal portion 40 of deployment mechanism 20 includes a rib 62 that is configured to protrude into a proximal coil of spring 56. Similarly, distal portion 42 of deployment mechanism 20 includes a rib 66 that is configured to protrude into a distal coil of spring 56. It will be appreciated, however, that a variety of alternative configurations for effecting communication or connection between spring 56 and deployment mechanism 20 exist, and any such alternatives may be used. In addition, it will be appreciated that any suitable alternative to spring 56 may be used, including but not limited to any other type of resilient member or members.

Figure 5:
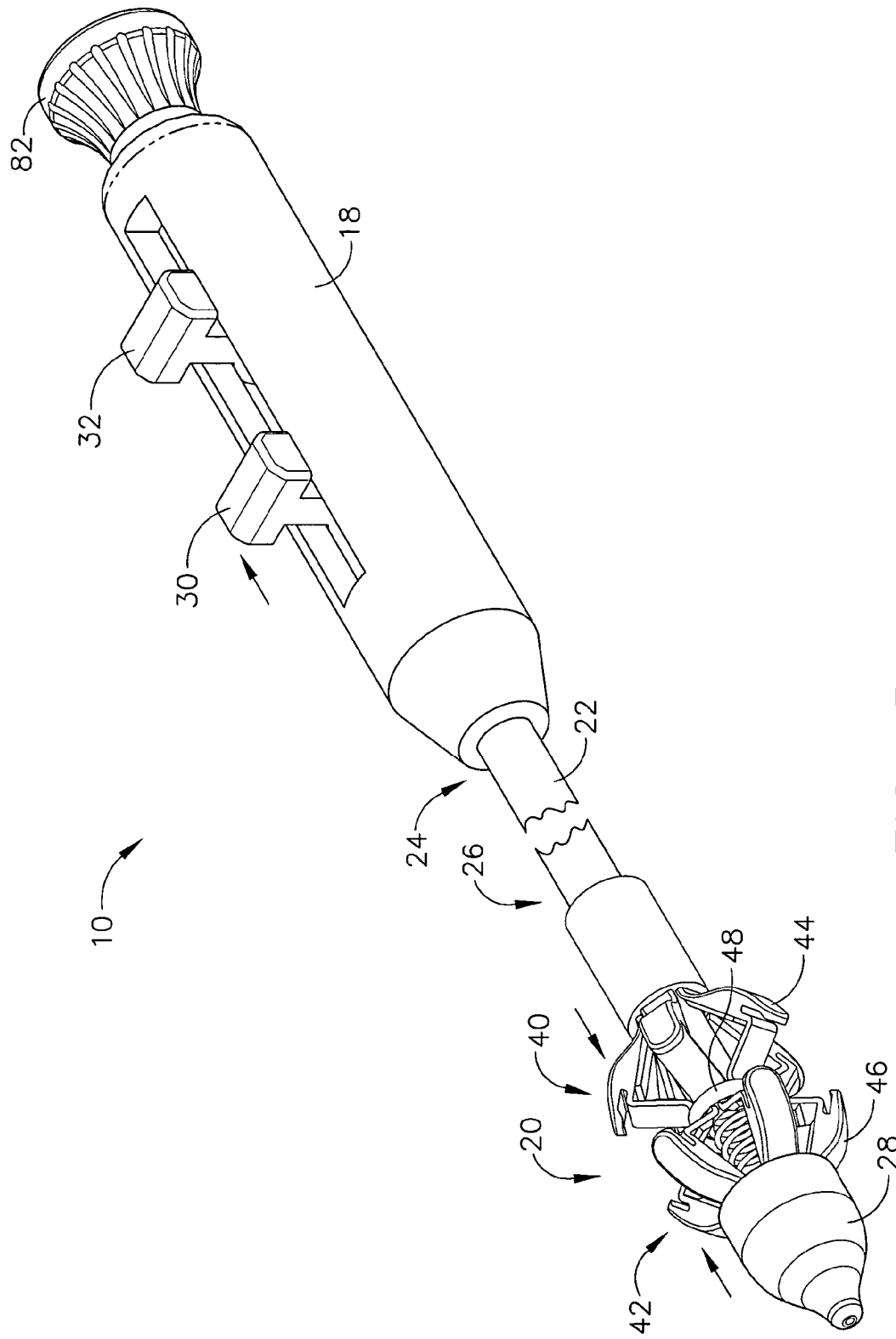
FIG. 5 is a perspective view of the device of FIG. 1 with the ring deployment mechanism in a partially actuated position.
Figure 6:
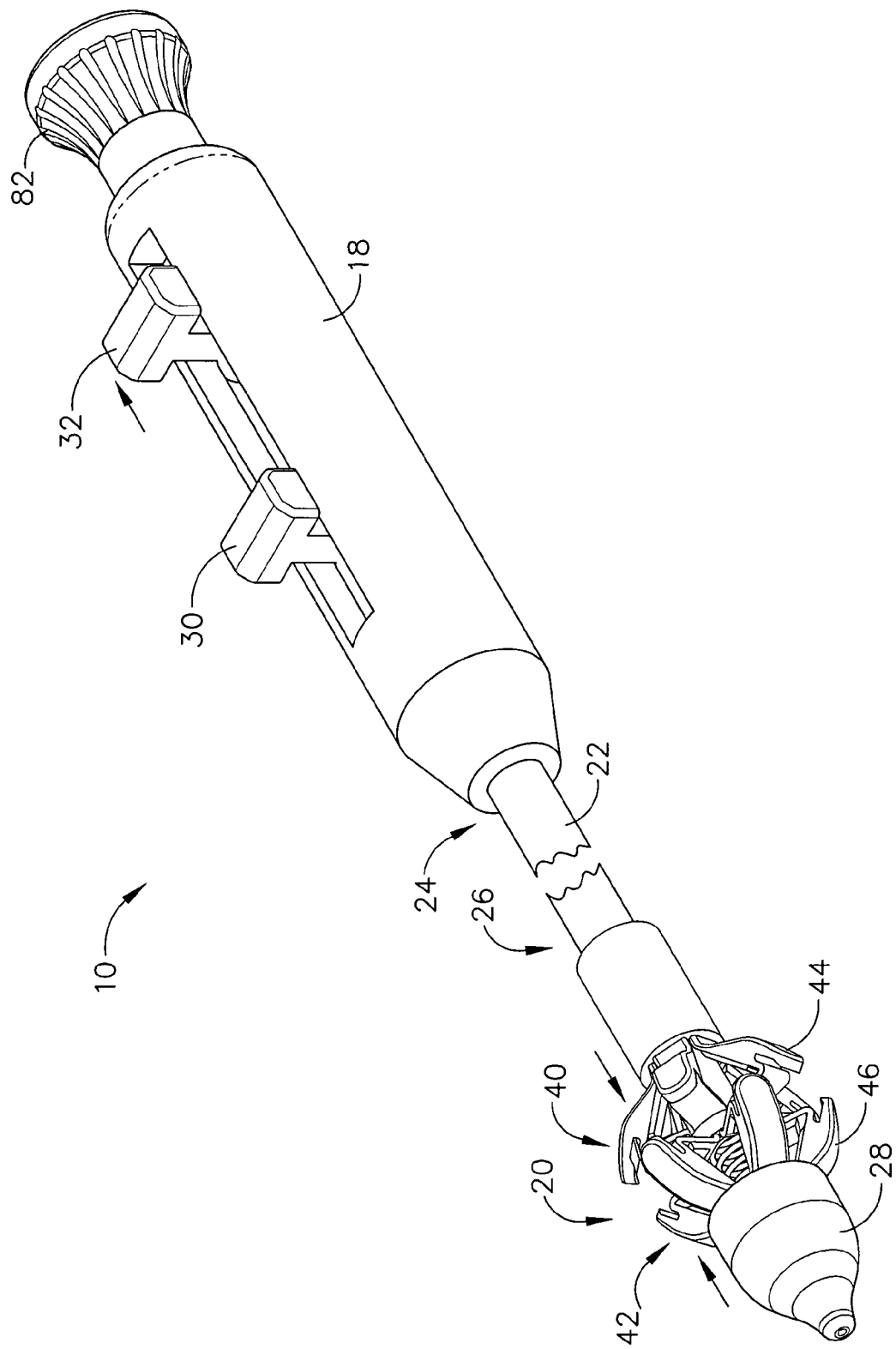
FIG. 6 is a perspective view of the device of FIG. 1 with the ring deployment mechanism in a fully actuated position.
Figure 9:
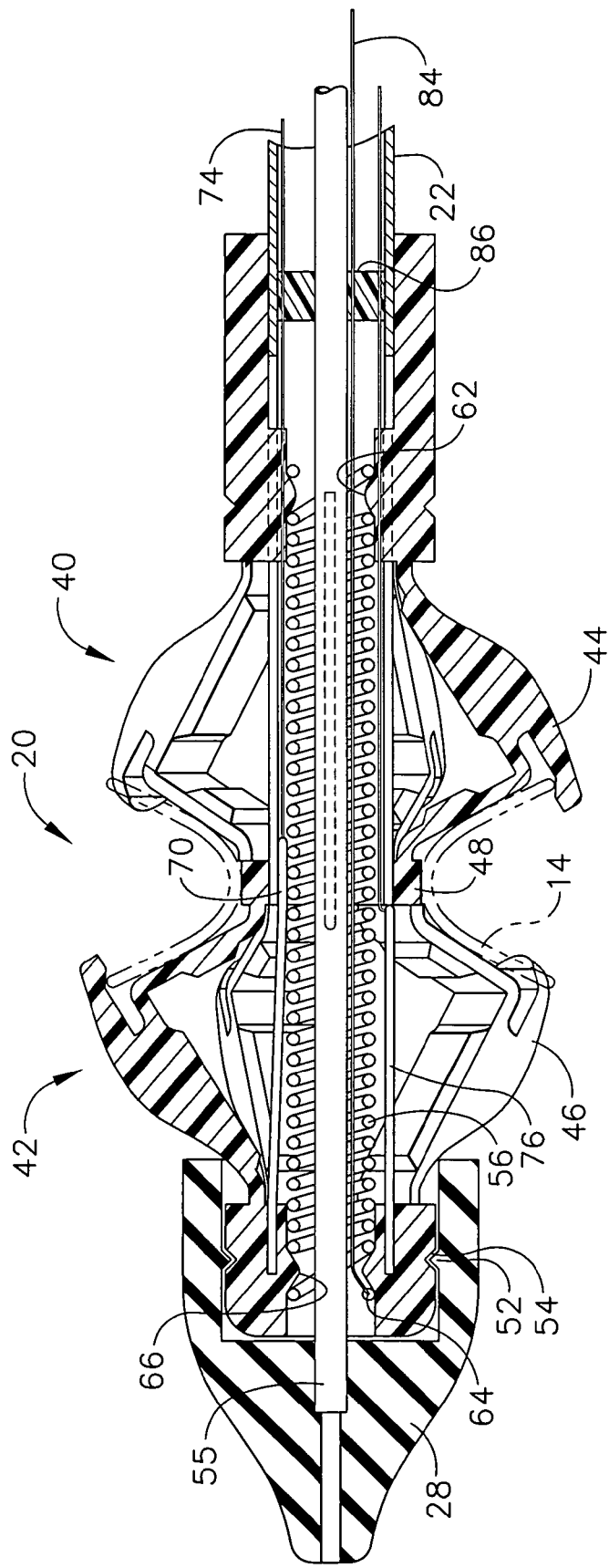
FIG. 9 is a cross-sectional view of the ring deployment mechanism of the device of FIG. 1 in the partially actuated position.
Figure 10:
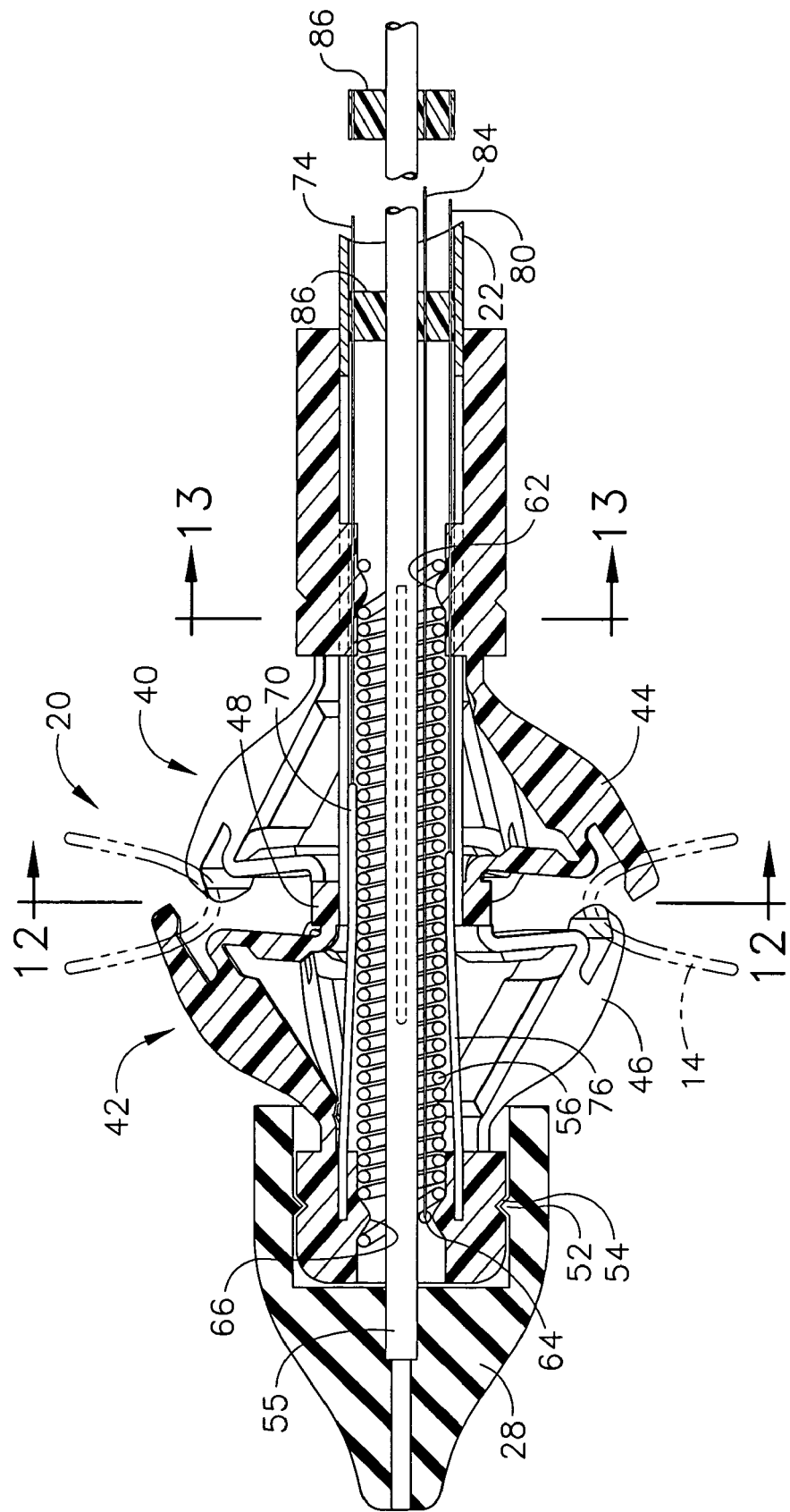
FIG. 10 is a cross-sectional view of the ring deployment mechanism of the device of FIG. 1 in the fully actuated position.

In the present example, extension spring 56 is biased to compress when proximal and distal fingers 44, 46 are in the unactuated position. An exemplary unactuated position is as shown in FIGS. 1 and 8. Because distal portion 42 of deployment mechanism 20 and mid-ring 48 are configured to move longitudinally with respect to the distal end of shaft 22, while proximal portion 40 of deployment mechanism 20 is rigidly attached to shaft 22, compression of spring 56 is operable to cause distal portion 42 and mid-ring 48 to move toward proximal portion 40. Due to the double-hinged relationship between both proximal and distal fingers 44, 46 and mid-ring 48, compression of distal portion 42 and mid-ring 48 toward proximal portion 40 may cause proximal fingers 44 and distal fingers 46 to articulate outwardly, actuating a proximal portion and a distal portion, respectively, of anastomotic ring 14. An exemplary intermediate step of such articulation or actuation of fingers 44, 46 is shown in FIGS. 5 and 9. An example of full articulation or actuation of fingers 44, 46 is shown in FIGS. 6 and 10.

Applier 10 is operable to maintain spring 56 in an extended position until the surgeon has appropriately positioned applier 10 at the anastomosis site. In the present example, applier 10 has a securing member comprising a substantially rigid strut 70. The distal end of strut 70 is hingedly or pivotally attached to distal portion 42 of deployment mechanism 20. When deployment mechanism 20 is in the unactuated position, strut 70 is in a set position, such that strut 70 is in communication with the distal surface of a rib member 92 of mid-ring 48 to prevent spring 56 from compressing. The proximal end of strut 70 is attached to first actuator 30 by a cable 74. The cable 74 passes through openings in bushings 86 and an opening in rib member 90 of proximal portion 40 of deployment mechanism 20. Of course, any suitable alternative to cable 74 may be used. First actuator 30 is operable to slide from a first, unactuated position proximally to a second, actuated position (FIG. 5), causing cable 74 to move proximally. As first actuator 30 is slid to the second, actuated position, cable 74 is configured to pivot strut 70 out of communication with the distal surface of rib member 92 of mid-ring 48, thereby allowing spring 56 to compress, which, as described above, will cause proximal and distal fingers 44, 46 to actuate.

Another strut 70 is positioned in the proximal portion 40 of deployment mechanism 20. Similar to the strut 70 in the distal portion 42, strut 70 in the proximal portion 40 is pivotable, and is configured to engage the proximal surface of a rib member 92 of mid-ring 48 to prevent spring 56 from compressing. Both struts 70 are connected to cable 74, which bifurcates to reach each strut 70, and is configured to pivot both struts 70 concomitantly in the same proximal motion of cable 74.

In another embodiment, struts 70 are located on opposing sides of the central longitudinal axis of shaft 22. Such strut 70 pairs may be positioned in both the distal and proximal portions 42, 40 of deployment mechanism 20.

Those of ordinary skill in the art will appreciate that, in order to ensure that anastomotic ring 14 is being properly deployed, it may be beneficial to effect deployment in two stages. In one embodiment, ring deployment mechanism 20 comprises a second strut 76. Second strut 76 is of shorter length than first strut 70, and is configured to encounter the distal surface of a rib member 92 of mid-ring 48 after disengagement of first strut 70 from a rib member 92 at a predetermined point in the articulation of fingers 44, 46, thereby preventing spring 56 from compressing further. Second strut 76 is in communication with second actuator 32 via a cable 80. Cable 80 passes through openings in bushings 86 and an opening in rib member 90 of proximal portion 40 of deployment mechanism 20. Second actuator 32 is operable to slide from a first, unactuated position proximally to a second, actuated position (FIG. 6), causing cable 80 to also move proximally. As second actuator 32 is slid to the second, actuated position, cable 80 is configured to pivot second strut 76 out of communication with stop 72, allowing spring 56 to fully compress, causing fingers 44, 46 to fully articulate and deploy anastomotic ring 14.

Another second strut 76 is positioned in the proximal portion 40 of deployment mechanism 20. Similar to the second strut 76 in the distal portion 42, second strut 76 in the proximal portion 40 is pivotable, and is configured to engage the proximal surface of a rib member 92 of mid-ring 48 to prevent spring 56 from compressing further. Both second struts 76 are connected to cable 80, which bifurcates to reach each second strut 76, and is configured to pivot both second struts 76 concomitantly in the same proximal motion of cable 74.

In another embodiment, second struts 76 are located on opposing sides of the central longitudinal axis of shaft 22. Such second strut 76 pairs may be positioned in both the distal and proximal portions 42, 40 of deployment mechanism 20. Where first and second strut pairs 70, 76 are positioned in each portion 40, 42 of deployment mechanism 20, the pairs may be angularly offset at any suitable distance.

Figure 7:
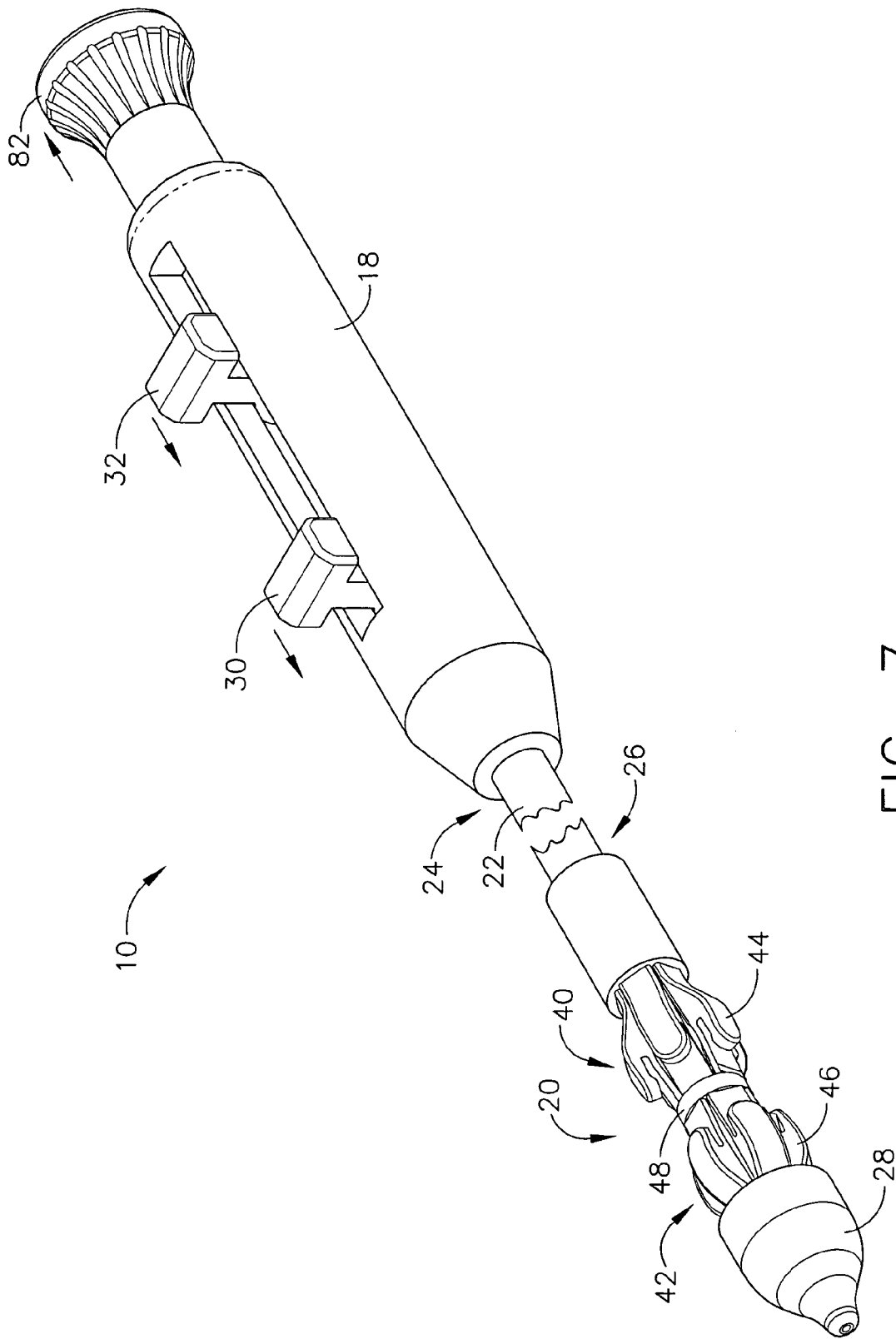
FIG. 7 is a perspective view of the device of FIG. 1 with the ring deployment mechanism returned to the unactuated position and with a spring actuator in the extended position.
Figure 11:
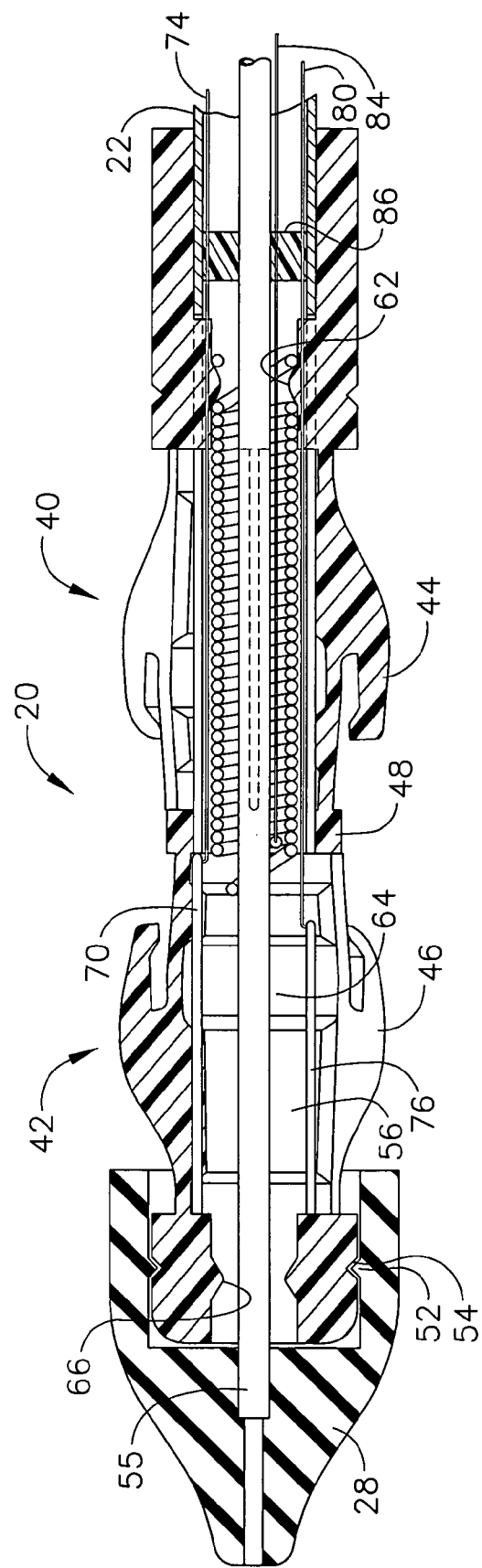
FIG. 11 is a cross-sectional view of the ring deployment mechanism the device of FIG. 1 returned to the unactuated position and with the spring extended by the spring actuator.

Referring now to FIGS. 7 and 11, after deployment of ring 14, applier 10 is operable to return fingers 44, 46 to the unactuated position for extraction of applier 10 from the anastomosis site. Applier 10 comprises a spring actuator 82. Spring actuator 82 is in communication with distal coil 64 of spring 56 by a connector 84. Spring actuator 82 is operable to move from a default position, in which connector 84 puts little or no force on spring 56, to an extended position (FIG. 7), in which connector 84 moves proximally, pulling distal coil 64 of spring 56 in the proximal direction (FIG. 11). When spring actuator 82 is moved to the extended position, distal coil 64 will disengage rib 66 of distal portion 42, substantially freeing deployment mechanism 20 from the compressive effect of spring 56. In the present example, the resilience of the material comprising deployment mechanism 20 will cause the deployment mechanism to extend distally when the spring 56 no longer exerts compressive forces on the deployment mechanism 20. Such distal self-extension of the deployment mechanism 20 will thereby result in fingers 44, 46 returning to a substantially unactuated position. Thus, movement of spring actuator 82 to the extended position is operable to allow proximal and distal fingers 44, 46 to return to a substantially unactuated position, thereby allowing applier 10 to be safely extracted from the patient.

It will be appreciated that any suitable alternative to struts 70, 76 and/or actuators 30, 32 may be used. Such alternatives and variations will be apparent to those of ordinary skill in the art.

For instance, in another embodiment, spring actuator 82 is in communication with rod 55. In this embodiment, spring actuator 82 is operable to be longitudinally advanced distally. Such distal advancement of spring actuator 82 will cause distal advancement of tip 28, against the compressive urging of spring 56, eventually resulting in the return of fingers 44, 46 to a substantially unactuated position. Spring actuator 82 may comprise a feature such that, upon sufficient distal advancement of spring actuator 82, the feature is configured to hold spring actuator 82 in place. In other words, the feature may prevent subsequent proximal movement of spring actuator 82 such that spring actuator 82 holds rod 55 to maintain a force that opposes the resilience of spring 56. Such a feature may comprise a protrusion that is configured to engage with a groove in the proximal end of handle 18 upon sufficient distal advancement of spring actuator 82 and rotation of spring actuator 82. With spring actuator 82, rod 55, and ring deployment mechanism 20 so held in place, applier 10 may be safely extracted from the patient.

In yet another alternate embodiment, which may be particularly suitable for, but need not be limited to, appliers 10 having a substantially rigid shaft 22, applier 10 lacks struts 70, 76, cables 80, and first and second actuators 30, 32. In this embodiment, handle 18, rod 55, spring actuator 82, and spring 56 are operable to effect actuation of ring deployment mechanism 20. The handle 18 has a cylindrical opening through which a proximal portion of the rod 55 is disposed. The sidewall of the cylindrical opening has a groove formed therein. The groove has a stair-like configuration, which extends longitudinally for a distance, than circumferentially for a distance, then longitudinally for a distance, and so forth. The proximal end of the rod 55 is fixedly attached to the spring actuator 82, such that rotation of spring actuator 82 with respect to rod 55 is substantially prevented, and they are operable to rotate concomitantly. A protrusion extends radially outward from a proximal portion of the rod 55. The protrusion is configured to engage the groove in the cylindrical opening of the handle 18. In this embodiment, rod 55 is free to rotate with respect to ring deployment mechanism 20. With ring deployment mechanism 20 in an unactuated state, rod 55 is in a first distal position, longitudinally held in place by engagement of the protrusion with a circumferential portion of the groove. Being so held in place, rod 55 resists the compressive urging of the spring 56.

In this alternate embodiment, upon rotation of spring actuator 82, protrusion in rod 55 reaches a longitudinal portion of the groove, which permits rod 55 to travel proximally to reach a second position, which further permits spring 56 to compress deployment mechanism 20 to a partially actuated position. Proximal movement of rod 55 stops when the protrusion reaches the next circumferential portion of the groove, at which point the user may again rotate the spring actuator 82 to make the protrusion reach the next longitudinal portion, which, when traversed by the protrusion, will permit the spring 56 to cause the deployment mechanism 20 to reach a fully actuated position. It will be appreciated that, upon complete actuation of the deployment mechanism 20, the deployment mechanism 20 may again be placed in the unactuated position through successive steps of rotation and distal advancement (against the urging of spring 56) of spring actuator 82. It will also be appreciated that the foregoing embodiment may be varied in any suitable way, including but not limited to the number of "stairs" or stages, the configuration of the groove, or groove-protrusion alternatives. For instance, each circumferential portion of the groove may have a longitudinal "hump," which will be engaged by the protrusion at the urging of the spring 56, such that the user must exert some distal force on spring actuator 82 in order to rotate spring actuator 82 to make protrusion traverse the circumferential portion of the groove. Still other variations will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument operable to implant an anastomotic ring, the instrument comprising:
    a handle;
    a ring deployment mechanism having a proximal portion, a distal portion, and a central portion, wherein the ring deployment mechanism is configured to receive and deploy an anastomotic ring, wherein the central portion comprises a rib member;
    an elongate shaft connecting the handle to the ring deployment mechanism;
    a first rigid member attached to the distal portion of the ring deployment mechanism and configured to engage the rib member of the central portion of the ring deployment mechanism;
    a second rigid member attached to the proximal portion of the ring deployment mechanism and configured to engage the rib member of the central portion of the ring deployment mechanism, wherein the second rigid member is shorter than the first rigid member;
    a first sliding actuating member configured to communicate with the first member via a cable, wherein the first sliding actuating member is configured such that sliding the first sliding actuating member from an unactuated position to an actuated position causes the first rigid member to disengage the rib member of the central portion of the ring deployment mechanism, wherein the second rigid member is configured to engage the rib member after the disengagement of the first rigid member and the rib member;
    a second sliding actuating member configured to communicate with the second rigid member via a cable, wherein the second sliding actuating member is configured such that sliding the second sliding actuating member from an unactuated position to an actuated position causes the second rigid member to disengage the rib member of the central portion of the ring deployment mechanism; and
    a resilient member in communication with the ring deployment mechanism, wherein the resilient member comprises a first end and a second end, wherein the resilient member is biased to urge the distal portion of the ring deployment mechanism toward the proximal portion of the ring deployment mechanism, wherein the first end of the resilient member is engaged with the distal portion of the ring deployment mechanism when the first sliding actuating member is in the unactuated position, the resilient member being moveable from a first position when the first actuating member is in the unactuated position to a second position when the first actuating member is in the actuated position, the resilient member being moveable from a second position when the second actuating member is in the unactuated position to a third position when the second actuating member is in the actuated position, wherein the resilient member is configured to actuate the ring deployment mechanism by moving from the first position to the second position and to the third position.

2. The instrument of claim 1, wherein the resilient member comprises a spring.

3. The instrument of claim 1, wherein the resilient member is biased to compress from the first position to the second position.

4. The instrument of claim 1, wherein the shaft is substantially flexible.

5. A surgical instrument operable to implant an anastomotic ring device, the instrument comprising:
    a handle;
    a ring deployment mechanism comprising a proximal portion, a distal portion, and a mid-ring, wherein the mid-ring has a distal end and a proximal end, the ring deployment mechanism being configured to receive and deploy an anastomotic ring device;
    a first rigid member attached to the distal portion of the ring deployment mechanism and configured to engage the distal end of the mid-ring, wherein the first rigid member comprises a strut pivotally attached to the distal portion of the ring deployment mechanism and configured to pivot away from the distal end of the mid-ring to disengage the mid-ring;
    a second rigid member attached to the proximal portion of the ring deployment mechanism and configured to engage the proximal end of the mid-ring, wherein the second rigid member comprises a strut pivotally attached to the proximal portion of the ring deployment mechanism and configured to pivot away from the proximal end of the mid-ring to disengage the mid-ring;
    a third rigid member attached to the distal portion of the ring deployment mechanism and configured to engage the distal end of the mid-ring, wherein the third rigid member comprises a strut pivotally attached to the distal portion of the ring deployment mechanism and configured to pivot away from the distal end of the mid-ring to disengage the mid-ring;

a fourth rigid member attached to the proximal portion of the ring deployment mechanism and configured to engage the proximal end of the mid-ring, wherein the fourth rigid member comprises a strut pivotally attached to the proximal portion of the ring deployment mechanism and configured to pivot away from the proximal end of the mid-ring to disengage the mid-ring;

a first sliding actuating member comprising a first cable, wherein the first sliding actuating member is configured to communicate with the first rigid member and the second rigid member via the first cable, wherein the first sliding actuating member is configured such that sliding the first actuating member from an unactuated position to an actuated position disengages the first rigid member and the second rigid member from the mid-ring, and such that sliding the first actuating member from an unactuated position to an actuated position engages the third rigid member and the fourth rigid member with the mid-ring;

a second sliding actuating member comprising a second cable, wherein the second sliding actuating member is configured to communicate with the third rigid member and the fourth rigid member via the second cable, wherein the second actuating member is configured such that sliding the second actuating member from an unactuated position to an actuated position respectively disengages the third rigid member and the fourth rigid member from the mid-ring;

an elongate shaft comprising a proximal portion and a distal portion, wherein the handle is connected to the proximal portion of the shaft, wherein the ring deployment mechanism is connected to the distal portion of the shaft;

a compressively-biased member positioned at the distal portion of the shaft, wherein the compressively-biased member comprises a distal end and a proximal end, the compressively-biased member being in communication with the ring deployment mechanism, wherein the distal end is engaged with the distal portion of the ring deployment mechanism, wherein the proximal end is engaged with the proximal portion of the ring deployment mechanism, wherein the compressively biased member is configured to urge the ring deployment mechanism to an actuated position; and a release member that is configured to move from a first position to a second position, wherein the release member is in communication with the distal end of the compressively-biased member when in the first position, wherein the release member is operable to be moved in a proximal direction to terminate the engagement between the compressively-biased member and the distal end of the ring deployment mechanism, wherein terminating the engagement between the ring deployment mechanism and the compressively-biased member is operable to release the ring deployment mechanism from the compressive effect of the compressively-biased member.

6. The instrument of claim 5, wherein the compressively-biased member comprises an extension spring.

7. The instrument of claim 5, wherein the proximal portion of the ring deployment mechanism is fixedly connected to the shaft.

8. The instrument of claim 7, wherein the compressively-biased member is configured to move the distal portion of the ring deployment mechanism and the mid-ring of the ring deployment mechanism toward the proximal portion of the ring deployment mechanism.

9. The instrument of claim 8, wherein the distal portion comprises distal fingers in a double-hinged relationship with the mid-ring of the ring deployment mechanism and the proximal portion of the ring deployment mechanism comprises proximal fingers in a double-hinged relationship with the mid-ring of the ring deployment mechanism.

10. The instrument of claim 9, wherein the distal portion of the ring deployment mechanism and the mid-ring of the ring deployment mechanism are configured to move away from the proximal portion when the release member is moved to the second position.

11. The instrument of claim 5, further comprising one or more blocking mechanisms, wherein each blocking mechanism is configured to resist the compressive urging of the compressively-biased member when each blocking member is in a set position.

12. The instrument of claim 11, further comprising at least one blocking member actuator, each blocking member actuator being operable to move at least one of the one or more blocking mechanisms from the set position.

13. The instrument of claim 1, wherein the first rigid member comprises a first strut.

14. The instrument of claim 13, wherein the first strut is configured to pivot to disengage the central portion of the ring deployment mechanism.

15. The instrument of claim 13, wherein the second rigid member comprises a second strut, wherein the second strut is configured to pivot away from the central portion of the ring deployment mechanism to disengage the central portion of the ring deployment mechanism.

16. The instrument of claim 5, wherein the elongate shaft defines a longitudinal axis, wherein the first rigid member and second rigid member extend in directions parallel to the longitudinal axis.

17. The instrument of claim 16, wherein the first rigid member is located at a first angular position relative to the longitudinal axis, wherein the second rigid member is located at a second angular position relative to the longitudinal axis, wherein the first and second angular positions are angularly spaced approximately 180° apart from one another relative to the longitudinal axis.

18. The instrument of claim 17, wherein the third and fourth rigid members are located at angular positions relative to the longitudinal axis such that the third and fourth rigid members are spaced approximately 180° apart from one another relative to the longitudinal axis, wherein the third and fourth rigid members are spaced approximately 90° apart from the first and second rigid members, respectively.

19. A surgical instrument operable to implant an anastomotic ring, the instrument comprising:

a handle;

a ring deployment mechanism having a proximal portion, a distal portion, and a central portion, wherein the ring deployment mechanism is configured to receive and deploy an anastomotic ring, wherein the central portion comprises a rib member;

an elongate shaft connecting the handle to the ring deployment mechanism;

a first rigid member attached to the distal portion of the ring deployment mechanism and configured to engage the rib member of the central portion of the ring deployment mechanism;

a second rigid member attached to the proximal portion of the ring deployment mechanism and configured to engage the rib member of the central portion of the ring deployment mechanism;

a first actuating member configured to communicate with the first member via a cable, wherein the first actuating member is configured such that moving the first actuating member from an unactuated position to an actuated position causes the first rigid member to disengage the rib member of the central portion of the ring deployment mechanism, wherein the second rigid member is configured to engage the rib member after the disengagement of the first rigid member and the rib member;

a second actuating member configured to communicate with the second rigid member via a cable, wherein the second actuating member is configured such that moving the second actuating member from an unactuated position to an actuated position causes the second rigid member to disengage the rib member of the central portion of the ring deployment mechanism;

a resilient member in communication with the ring deployment mechanism, wherein the resilient member comprises a first end and a second end, wherein the first end is engaged with the distal portion of the ring deployment mechanism when the first actuating member is in the unactuated position, the resilient member being moveable from a first position when the first actuating member is in the unactuated position to a second position when the first actuating member is in the actuated position, the resilient member being moveable from a second position when the second actuating member is in the unactuated position to a third position when the second actuating member is in the actuated position, wherein the resilient member is configured to actuate the ring deployment mechanism by moving from the first position to the second position and to the third position; and a spring release in communication with the first end of the resilient member, the spring release being moveable from a first position to a second position, wherein the movement of the spring release from the first position to the second position causes the first end of the resilient member to disengage the distal portion of the ring deployment mechanism, wherein movement of the spring release from the first position to the second position is operable to substantially release the ring deployment mechanism from forces exerted by the resilient member.

* * * * *